United States Patent
Fukuda et al.

(10) Patent No.: US 10,905,318 B2
(45) Date of Patent: Feb. 2, 2021

(54) ENDOSCOPE SYSTEM

(71) Applicant: HOYA CORPORATION, Tokyo (JP)

(72) Inventors: Masaaki Fukuda, Tokyo (JP); Yoshimi Obara, Tokyo (JP); Toru Chiba, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 48 days.

(21) Appl. No.: 16/333,197

(22) PCT Filed: Oct. 12, 2017

(86) PCT No.: PCT/JP2017/037004
§ 371 (c)(1),
(2) Date: Mar. 13, 2019

(87) PCT Pub. No.: WO2018/070474
PCT Pub. Date: Apr. 19, 2018

(65) Prior Publication Data
US 2019/0223705 A1 Jul. 25, 2019

(30) Foreign Application Priority Data
Oct. 14, 2016 (JP) ................... 2016-202632

(51) Int. Cl.
*A61B 1/06* (2006.01)
*A61B 1/045* (2006.01)
(Continued)

(52) U.S. Cl.
CPC ............ *A61B 1/045* (2013.01); *A61B 1/0638* (2013.01); *A61B 1/0676* (2013.01); *G02B 23/24* (2013.01);
(Continued)

(58) Field of Classification Search
CPC ......... A61B 1/0638; A61B 1/00; A61B 1/045; A61B 1/0676; A61B 1/00009;
(Continued)

(56) References Cited

U.S. PATENT DOCUMENTS

2012/0220840 A1* 8/2012 Morita ................ A61B 1/0638
600/317
2014/0010424 A1 1/2014 Chiba et al.
(Continued)

FOREIGN PATENT DOCUMENTS

| DE | 112017004417 | 5/2019 |
| DE | 112017004418 | 5/2019 |

(Continued)

OTHER PUBLICATIONS

DE112017005214.9, Office Action dated Sep. 16, 2019 (13 pp.).
(Continued)

*Primary Examiner* — Leon Viet Q Nguyen
(74) *Attorney, Agent, or Firm* — Kilpatrick Townsend & Stockton LLP

(57) ABSTRACT

An endoscope system includes a processor and displays a distribution image of living substance feature amounts obtained from an imaged image of a living tissue. The processor calculates the living substance feature amount in the living tissue, for example, an amount of hemoglobin and oxygen saturation of the hemoglobin using components of color image data of the living tissue illuminated with at least two lights, generates the feature amount distribution image illustrating a distribution of the living substance feature amounts, and controls display of the feature amount distribution image in order to display the generated feature amount distribution image so as to be superimposed on the image of the living tissue.

15 Claims, 5 Drawing Sheets

(51) Int. Cl.
    *G02B 23/26*    (2006.01)
    *G02B 23/24*    (2006.01)
    *A61B 1/00*     (2006.01)

(52) U.S. Cl.
    CPC .......... *G02B 23/26* (2013.01); *A61B 1/00009* (2013.01); *G02B 23/2461* (2013.01)

(58) Field of Classification Search
    CPC ...... A61B 1/0008; G02B 23/24; G02B 23/26; G02B 23/2461
    See application file for complete search history.

(56) References Cited

U.S. PATENT DOCUMENTS

| | | |
|---|---|---|
| 2015/0193929 A1 | 7/2015 | Ikemoto |
| 2015/0238086 A1 | 8/2015 | Saito |
| 2015/0238127 A1* | 8/2015 | Saito .................... H04N 5/3575 600/339 |
| 2016/0058274 A1 | 3/2016 | Chiba |
| 2016/0120449 A1 | 5/2016 | Chiba |
| 2016/0146723 A1 | 5/2016 | Chiba |
| 2017/0098301 A1 | 4/2017 | Ikemoto et al. |
| 2019/0216305 A1 | 7/2019 | Fukuda |
| 2019/0223703 A1 | 7/2019 | Fukuda |

FOREIGN PATENT DOCUMENTS

| | | |
|---|---|---|
| JP | H09-173285 A   | 7/1997 |
| JP | 2011-104016 A  | 6/2011 |
| JP | 2013-240401 A  | 12/2013 |
| JP | 2014003462 A   | 1/2014 |
| JP | 2014-018332 A  | 2/2014 |
| JP | 2015136397 A   | 7/2015 |
| JP | 2015-160012 A  | 9/2015 |
| JP | 2015-160013 A  | 9/2015 |
| JP | 2016-052391 A  | 4/2016 |
| JP | 2016-097067 A  | 5/2016 |
| WO | 2012/132571 A1 | 10/2012 |
| WO | 2014/192781 A1 | 12/2014 |
| WO | 2016/136698 A1 | 9/2016 |

OTHER PUBLICATIONS

PCT/JP2017/037004, English Translation of International Search Report dated Jan. 9, 2018, 2 pages.

JP2018-545048, "Notice of Reasons for Refusal" with Machine Translation, dated Mar. 17, 2020, 6 pages.

* cited by examiner

ENDOSCOPE SYSTEM

CROSS-REFERENCE TO RELATED APPLICATIONS

This application is a 371 U.S. National Phase of PCT International Application No. PCT/JP2017/037004, filed on Oct. 12, 2017, which claims benefit and priority to Japanese patent application No. 2016-202632, filed Oct. 14, 2016, and which is incorporated by reference herein in its entirety.

TECHNICAL FIELD

The present disclosure relates to an endoscope system for displaying a feature amount distribution image illustrating a distribution of living substance feature amounts on the basis of image data generated by imaging a living tissue.

BACKGROUND ART

An endoscope system having a function of obtaining information on a living substance in a living tissue being an object, for example, an amount of hemoglobin and oxygen saturation of hemoglobin from the image data obtained by the endoscope and displaying an image of the information is known. An example of such an endoscope system is disclosed in Patent Literature 1.

An endoscope system disclosed in Patent Literature 1 includes imaging means for obtaining spectral image data by imaging a spectral image of a predetermined wavelength region in a body cavity, processing means for performing predetermined processing on the spectral image data to generate composite image data in which a feature amount of a living tissue, for example, oxygen saturation is emphasized, and display means for displaying a screen based on the composite image data. The endoscope system may display the composite image as an image for specifying a lesion so as to be distinguished from a healthy site.

CITATION LIST

Patent Literature

Patent Literature 1: JP 2013-240401 A

SUMMARY OF INVENTION

Technical Problem

The endoscope system is desired to be able to determine presence or absence of the non-healthy site, for example, the presence or absence of the lesion and find its distribution in the living tissue. Especially, it is preferable to find a plurality of types of non-healthy sites, and further a plurality of types of suspected sites as the lesions in one observation in view of shortening procedure time and decreasing a burden on a patient. That is, in the endoscope system, it is preferable to display an image in which a plurality of suspected sites as the lesions may be found by one observation as for a plurality of types of non-healthy sites. However, in the above-described endoscope system, such image display is not performed.

The present disclosure is achieved in view of the above-described circumstances, and an object thereof is to provide an endoscope system which performs image display capable of finding a plurality of types of non-healthy sites with different ranges of living substance feature amounts by one observation.

Solution to Problem

The present disclosure includes the following modes.
(Mode 1)
An endoscope system including:
a light source device configured to emit at least two lights having different wavelength bands;
an endoscope including an imaging unit including an imaging element configured to generate color image data corresponding to each light by imaging a living tissue illuminated with the at least two lights;
a processor including a feature amount obtaining unit configured to calculate a living substance feature amount in the living tissue by using a component of the color image data to generate a feature amount distribution image illustrating a distribution of living substance feature amounts and an image display control unit configured to control display of the feature amount distribution image; and
an image display device configured to display the feature amount distribution image so as to be superimposed on an image of the living tissue,
in which the image display control unit is configured to take out an image of a first distribution of a first non-healthy site illustrating a distribution of first feature amount ranges different from living substance feature amounts of a healthy site and an image of a second distribution of a second non-healthy site illustrating a distribution of second feature amount ranges different from the first feature amount ranges and different from the living substance feature amounts of the healthy site out of the distribution of the living substance feature amounts from the distribution of the living substance feature amounts as the feature amount distribution image, and
the image display device is configured to identifiably display the image of the first distribution and the image of the second distribution so as to be superimposed on the image of the living tissue as the feature amount distribution image.
(Mode 2)
An endoscope system including:
a light source device configured to emit at least two lights having different wavelength bands;
an endoscope including an imaging unit including an imaging element configured to generate color image data corresponding to each light by imaging a living tissue illuminated with the at least two lights;
a processor including a feature amount obtaining unit configured to calculate an amount of hemoglobin and oxygen saturation of the hemoglobin in the living tissue by using a component of the color image data to generate an oxygen saturation distribution image illustrating a distribution of the oxygen saturation and an image display control unit configured to control display of the oxygen saturation distribution image; and
an image display device configured to display the oxygen saturation distribution image so as to be superimposed on the image of the living tissue,
in which the image display control unit is configured to take out an image of a first distribution of a first non-healthy site illustrating a distribution of first oxygen saturation ranges different from oxygen saturation of a healthy site and an image of a second distribution of a second non-healthy site illustrating a distribution of second oxygen saturation ranges different from the first oxygen saturation ranges and different from the oxygen saturation of the healthy site out of the distribution of the oxygen saturation from the distribution of the oxygen saturation as the oxygen saturation distribution image, and the image display device is configured to identifiably display the image of the first distribution and the image of the second distribution so as to be superimposed on the image of the living tissue as the oxygen saturation distribution image.

(Mode 3)

The endoscope system according to the mode 2, in which the image display control unit is configured to take out the image of the first distribution and the image of the second distribution so as to satisfy a fact that the amount of hemoglobin in each pixel position of the image of the first distribution and the image of the second distribution is equal to or larger than an amount determined in advance.

(Mode 4)

The endoscope system according to the mode 2 or 3, in which the feature amount obtaining unit includes a hemoglobin amount calculating unit configured to calculate the amount of hemoglobin on the basis of a first ratio between components of the color image data of the living tissue illuminated with different lights and an oxygen saturation calculating unit configured to calculate the oxygen saturation of hemoglobin on the basis of a second ratio between the components of the color image data and the amount of hemoglobin, and the image display control unit is configured to adjust transmissivity of a pixel displayed so as to be superimposed on the image of the living tissue as for the pixel in which a value of the second ratio is deviated from an allowable range of the second ratio determined according to the amount of hemoglobin.

(Mode 5)

The endoscope system according to any one of the modes 2 to 4, in which the light source device is configured to emit at least three or more lights including first light, second light, and third light having different wavelength bands, the imaging unit is configured to generate first color image data corresponding to the first light, second color image data corresponding to the second light, and third color image data corresponding to the third light by imaging the living tissue illuminated with the first light, the second light, and the third light, the feature amount obtaining unit includes the hemoglobin amount calculating unit configured to calculate the amount of hemoglobin on the basis of the first ratio between the components of the color image data of the living tissue illuminated with different lights and the oxygen saturation calculating unit configured to calculate the oxygen saturation of hemoglobin on the basis of the second ratio between the components of the color image data and the amount of hemoglobin, the first ratio is the ratio between a component of the first color image data and a component of the second color image data, and the second ratio is the ratio between the component of the second color image data and a component of the third color image data.

(Mode 6)

The endoscope system according to the mode 5, in which the hemoglobin amount calculating unit is configured to calculate the amount of hemoglobin by using a ratio between a luminance component of the second color image data and an R component of the first color image data or a total components of the R component and a G component as the first ratio.

(Mode 7)

The endoscope system according to the mode 5 or 6, in which the oxygen saturation calculating unit is configured to calculate the oxygen saturation of hemoglobin on the basis of the second ratio and the amount of hemoglobin by using a ratio between a luminance component of the third color image data and the luminance component of the second color image data as the second ratio.

(Mode 8)

The endoscope system according to any one of the modes 5 to 7, in which the wavelength band of the first light is wider than the wavelength band of the second light and the wavelength band of the third light and the wavelength band of the second light is wider than the wavelength band of the third light, and the wavelength band of the first light includes a wavelength band in which the component of the first color image data is not sensitive to a change in the amount of hemoglobin in the living tissue.

(Mode 9)

The endoscope system according to any one of the modes 5 to 8, in which the wavelength band of the second light includes a wavelength band in which the component of the second color image data is sensitive to the change in the amount of hemoglobin of the living tissue but is not sensitive to a change in the oxygen saturation.

(Mode 10)

The endoscope system according to any one of the modes 5 to 9, in which the wavelength band of the third light includes a wavelength band in which the component of the third color image data is not sensitive to the change in the amount of hemoglobin of the living tissue but is sensitive to the change in the oxygen saturation.

(Mode 11)

The endoscope system according to any one of the modes 5 to 10, in which the second light is filtered light of the first light obtained by transmitting a first wavelength band within a range of 500 nm to 600 nm out of the wavelength band of the first light by an optical filter, and the third light is filtered light of the first light obtained by transmitting a second wavelength band narrower than the first wavelength band within a range of the first wavelength band by an optical filter.

Advantageous Effects of Invention

According to the above-described endoscope system, it is possible to find a plurality of types of non-healthy sites with different ranges of living substance feature amounts at one observation.

DESCRIPTION OF EMBODIMENTS

Figure 1:
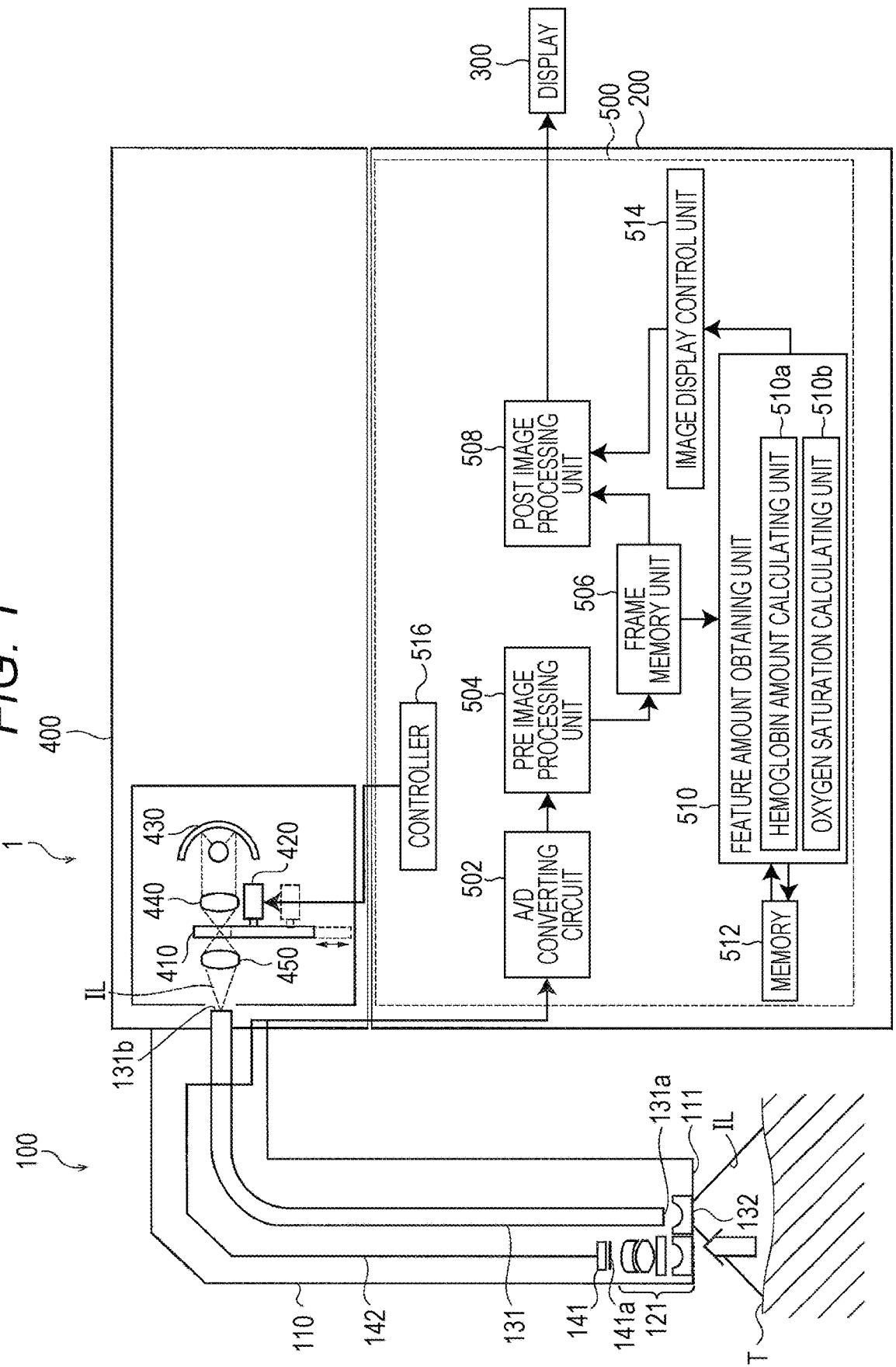
FIG. 1 is a block diagram of a configuration of an example of an endoscope system according to one embodiment.

An endoscope system according to an embodiment hereinafter described is a system which quantitatively calculates a living substance feature amount in a living tissue on the basis of a plurality of color image data obtained by imaging while illuminating the living tissue as an object with lights having different wavelength bands to image and displays a feature amount distribution image illustrating a distribution of the living substance feature amounts. For example, a system which displays an oxygen saturation distribution image is included. In the following description, an amount and oxygen saturation of hemoglobin are described as examples of the living substance feature amount, but the feature amount may be other than them. Also, since a color of the living substance in a non-healthy site is different from a color in a healthy site, as the living substance feature amount, that with which gas phase, saturation, or brightness of the living tissue changes identifiably by the living substance feature amount may be used, for example.

According to the endoscope system of one embodiment, by imaging the living tissue illuminated with at least two lights having different wavelength bands emitted from a light source device by an imaging element, the imaging element generates color image data of an image of the living tissue corresponding to each light. A processor calculates the living substance feature amount (for example, amount of hemoglobin and oxygen saturation of hemoglobin) in the living tissue using components of the generated color image data and generates the feature amount distribution image (for example, oxygen saturation distribution image) indicating the distribution of the living substance feature amounts (for example, oxygen saturation). The processor controls display of the feature amount distribution image (for example, oxygen saturation distribution image) in the image display device.

In the control of the display of the feature amount distribution image (for example, oxygen saturation distribution image), an image of a first distribution of a first non-healthy site illustrating a distribution of first feature amount ranges (for example, oxygen saturation ranges) different from the living substance feature amount of the healthy site and an image of a second distribution of a second non-healthy site illustrating a distribution of second feature amount ranges (for example, second oxygen saturation ranges) different from the first feature amount ranges (for example, first oxygen saturation ranges) and different from the living substance feature amount of the healthy site out of the distribution of the living substance feature amounts (for example, oxygen saturation) are taken out from the distribution of the living substance feature amounts (for example, oxygen saturation) in the feature amount distribution image (for example, oxygen saturation distribution image). The image display device displays the image of the first distribution and the image of the second distribution identifiably so as to be superimposed on the image of the living tissue as the feature amount distribution image (for example, oxygen saturation distribution image).

(Configuration of Endoscope System)

FIG. 1 is a block diagram illustrating a configuration of an endoscope system 1 according to one embodiment. The endoscope system 1 includes an electronic endoscope (endoscope) 100, a processor 200, a display 300, and a light source device 400. The electronic endoscope 100 and the display 300 are detachably connected to the processor 200. The processor 200 includes an image processing unit 500. The light source device 400 is detachably connected to the processor 200.

The electronic endoscope 100 includes an insertion tube 110 to be inserted into the body of a subject. A light guide 131 extending substantially over an entire length of the insertion tube 110 is provided in the insertion tube 110. A distal end 131a being one end of the light guide 131 is located on a distal end of the insertion tube 110, that is, in the vicinity of an insertion tube distal end 111, and a proximal end 131b being the other end of the light guide 131 is located in a connecting portion to the light source device 400. Therefore, the light guide 131 extends from the connecting portion to the light source device 400 to the vicinity of the insertion tube distal end 111.

The light source device 400 includes, as a light source, a light source lamp 430 which generates light having a large light volume such as a xenon lamp. The light emitted from the light source device 400 is incident on the proximal end 131b of the light guide 131 as illumination light IL. The light incident on the proximal end 131b of the light guide 131 passes through the light guide 131 to be guided to the distal end 131a thereof and emitted from the distal end 131a. A light distributing lens 132 arranged so as to be opposed to the distal end 131a of the light guide 131 is provided on the insertion tube distal end 111 of the electronic endoscope 100. The illumination light IL emitted from the distal end 131a of the light guide 131 passes through the light distributing lens 132 and illuminates a living tissue T in the vicinity of the insertion tube distal end 111.

An objective lens group 121 and an imaging element 141 are provided on the insertion tube distal end 111 of the electronic endoscope 100. The objective lens group 121 and the imaging element 141 form an imaging unit. Out of the illumination light IL, light reflected or scattered on a surface of the living tissue T is incident on the objective lens group 121, condensed, and forms an image on a light receiving surface of the imaging element 141. As the imaging element 141, a known imaging element such as a charge coupled device (CCD) image sensor for imaging a color image including a color filter 141a on a light receiving surface thereof, or a complementary metal oxide semiconductor (CMOS) image sensor may be used.

Figure 2:
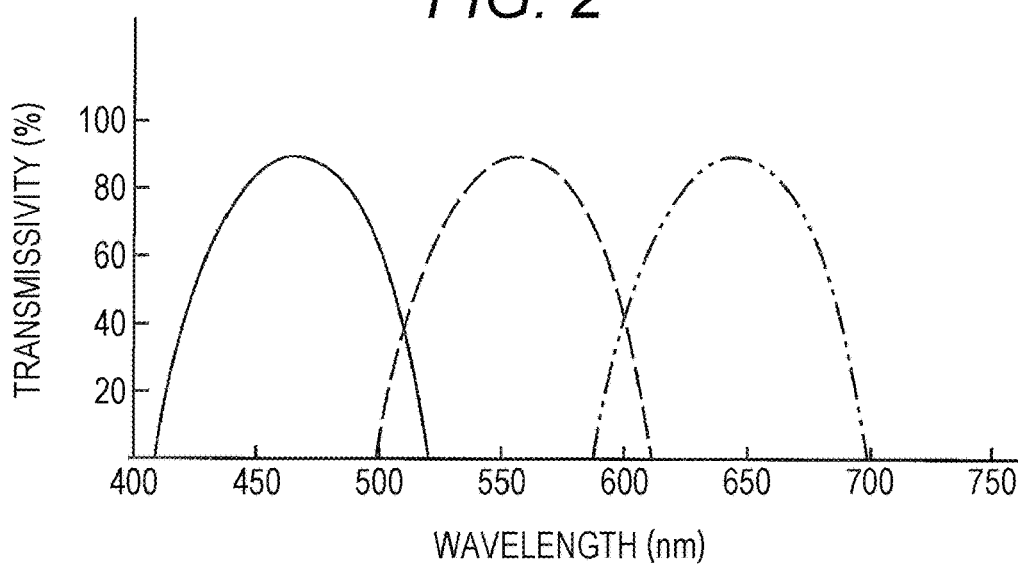
FIG. 2 is a view illustrating an example of spectral characteristics of red (R), green (G), and blue (B) filters of an imaging element used in one embodiment.

The color filter 141a on which an R color filter which transmits red light, a G color filter which transmits green light, and a B color filter which transmits blue light are arranged is a so-called on-chip filter directly formed on the respective light receiving elements of the imaging element 141. FIG. 2 is a view illustrating an example of spectral characteristics of red (R), green (G), and blue (B) filters of the imaging element used in this embodiment. The R color filter of this embodiment is a filter which transmits light having a wavelength longer than about 570 nm (for example, 580 nm to 700 nm), the G color filter is a filter which transmits light having a wavelength of about 500 nm to 620 nm, and the B color filter is a filter which transmits light having a wavelength shorter than about 530 nm (for example, 420 nm to 520 nm).

The imaging element 141 is imaging means which images the living tissue T illuminated with each of a plurality of lights and generates color image data corresponding to each light, image data generating means which generates the color image data corresponding to the light reflected or scattered on the living tissue T by illuminating the living tissue T by a plurality of lights having different wavelength ranges. The imaging element 141 is controlled to drive in synchronization with the image processing unit 500 to be described later, and periodically outputs (for example, at an interval of 1/30 seconds) the color image data corresponding to the image of the living tissue T formed on the light receiving surface. The color image data output from the imaging element 141 is transmitted to the image processing unit 500 of the processor 200 via a cable 142.

The image processing unit 500 mainly includes an A/D converting circuit 502, a pre-image processing unit 504, a frame memory unit 506, a post-image processing unit 508, a feature amount obtaining unit 510, a memory 512, an image display control unit 514, and a controller 516.

The A/D converting circuit 502 A/D converts the color image data input from the imaging element 141 of the electronic endoscope 100 via the cable 142 and outputs digital data. The digital data output from the A/D converting circuit 502 is transmitted to the pre-image processing unit 504. The A/D converting circuit 502 may also be provided in the electronic endoscope (endoscope) 100.

The pre-image processing unit 504 generates the color image data of R, G, and B components forming the image from the digital data by a demosaic process from R digital image data imaged by the light receiving element in the imaging element 141 on which the R color filter is mounted, G digital image data imaged by the light receiving element in the imaging element 141 on which the G color filter is mounted, and B digital image data imaged by the light receiving element in the imaging element 141 on which the B color filter is mounted. Furthermore, the pre-image processing unit 504 is a portion which performs predetermined signal processing such as color correction, matrix calculation, and white balance correction on the generated R, G, and B color image data.

The frame memory unit 506 temporarily stores the color image data of each image imaged by the imaging element 141 and subjected to the signal processing.

The post-image processing unit 508 reads the color image data stored in the frame memory unit 506 or performs signal processing (γcorrection or the like) on image data generated by the image display control unit 514 to be described later, and generates screen data for display. The image data generated by the image display control unit 514 includes data of the distribution image of the feature amount such as the oxygen saturation distribution image illustrating the distribution of the oxygen saturation of hemoglobin of the living tissue T as described later. The generated screen data (video format signal) is output to the display 300. As a result, the image of the living tissue T, the distribution image of the feature amount of the living tissue T and the like are displayed on a screen of the display 300.

In response to an instruction of the controller 516, the feature amount obtaining unit 510 calculates the amount of hemoglobin and the oxygen saturation of hemoglobin of the imaged living tissue T as the living substance feature amounts (hereinafter simply referred to as "feature amounts") and generates the distribution image on the image of the imaged living tissue T of the feature amounts, that is, the distribution image illustrating the distribution of the amount of hemoglobin and the oxygen saturation distribution image illustrating the distribution of the oxygen saturation of hemoglobin as described later.

Since the feature amount obtaining unit 510 calculates the feature amount by calculating using the color image data of the living tissue T illuminated with a plurality of lights having different wavelength bands, this calls the color image data and various pieces of information used by the feature amount obtaining unit 510 from the frame memory unit 506 or the memory 512.

The image display control unit 514 controls to display the oxygen saturation distribution image of hemoglobin generated by the feature amount obtaining unit 510 so as to be superimposed on the image of the imaged living tissue T. At that time, the image display control unit 514 determines whether there is a pixel having a pixel value within a range of the oxygen saturation of the non-healthy site, that is, within the oxygen saturation range out of the range of the oxygen saturation in the normal living tissue in the oxygen saturation distribution image, takes out distribution of a plurality of types of oxygen saturation ranges (at least one of an upper limit value and a lower limit value of the range is different) according to a determination result, and controls the oxygen saturation distribution image so as to display the image of the taken out distribution so as to be superimposed on the image of the living tissue. This point is to be described later.

The controller 516 issues an operation instruction and controls operation of each unit of the image processing unit 500 as well as issuing an operation instruction and controlling operation of each unit of the electronic endoscope 100 including the light source device 400 and the imaging element 141.

Note that the feature amount obtaining unit 510 and the image display control unit 514 may be configured by software modules which perform the above-described functions by activating and executing a program on a computer, or may be configured by hardware.

In this manner, the processor 200 has a function of processing the color image data output from the imaging element 141 of the electronic endoscope 100 and a function of issuing the instruction and controlling the operation of the electronic endoscope 100, the light source device 400, and the display 300.

The light source device 400 emits at least two lights having different wavelength bands. Specifically, the light source device 400 is light emitting means which emits first light, second light, and third light, and allows the first light, the second light, and the third light to be incident on the light guide 131. The light source device 400 emits the first light, the second light, and the third light having different wavelength bands, but in another embodiment, four or more lights may be emitted. In this case, the fourth light may be the light having the same wavelength band as that of the first light. The light source device 400 includes, in addition to the light source lamp 430, a condenser lens 440, a rotary filter 410, a filter control unit 420, and a condenser lens 450. Light which is substantially parallel light emitted from the light source lamp 430 is, for example, white light, and this is condensed by the condenser lens 440, passes through the rotary filter 410, condensed again by the condenser lens 450, and is incident on the proximal end 131b of the light guide 131. Note that the rotary filter 410 is movable between a position on an optical path of the light emitted from the light source lamp 430 and a retreating position outside the optical path by a moving mechanism not illustrated such as a linear guideway. Since the rotary filter 410 includes a plurality of filters having different transmission characteristics, the wavelength band of the light emitted from the light source device 400 varies depending on a type of the rotary filter 410 crossing the optical path of the light emitted from the light source lamp 430.

Note that the configuration of the light source device 400 is not limited to that illustrated in FIG. 1. For example, a lamp which generates convergent light in place of parallel light may be adopted as the light source lamp 430. In this case, for example, a configuration in which the light emitted from the light source lamp 430 is condensed in front of the condenser lens 440 to be incident on the condenser lens 440 as diffusion light may also be adopted. In addition, it is also possible to adopt a configuration in which the substantially parallel light generated by the light source lamp 430 is directly incident on the rotary filter 410 without using the condenser lens 440. Also, in a case of using the lamp which generates the convergent light, a configuration may be adopted in which a collimator lens is used in place of the condenser lens 440 to allow the light to be incident on the rotary filter 410 in a state of the substantially parallel light. For example, in a case of using an interference type optical filter such as a dielectric multilayer film filter as the rotary filter 410, it is possible to obtain a more excellent filter characteristic by making an incident angle of light on the optical filter uniform by allowing the substantially parallel light to be incident on the rotary filter 410. Also, a lamp which generates divergent light may be adopted as the light source lamp 430. In this case also, it is possible to adopt a configuration of allowing the substantially parallel light to be incident on the rotary filter 410 by using a collimator lens in place of the condenser lens 440.

The light source device 400 is configured to emit a plurality of lights of different wavelength bands by allowing the light emitted from one light source lamp 430 to pass through the optical filter; however, it is also possible to use a plurality of lights having different wavelength bands, for example, a semiconductor light source such as a light emitting diode and a laser device which outputs laser light as the light source of the light source device 400 in place of the light source lamp 430. In this case, it is also possible that the rotary filter 410 is not used. In addition, the light source device 400 may be configured, for example, to emit synthesized white light including excitation light of a predetermined wavelength band and fluorescence excited and emitted by the excitation light and light of a predetermined narrow wavelength band separately. The configuration of the light source device 400 is not especially limited as long as this emits a plurality of lights having different wavelength bands.

The rotary filter 410 is a disk-shaped optical unit including a plurality of optical filters, and is configured such that a passing wavelength band of light is switched in accordance with a rotation angle. The rotary filter 410 of this embodiment includes three optical filters having different passing wavelength bands, but this may also be provided with four, five, or six or more optical filters. The rotation angle of the rotary filter 410 is controlled by the filter control unit 420 connected to the controller 516. When the controller 516 controls the rotation angle of the rotary filter 410 via the filter control unit 420, the wavelength band of the illumination light IL supplied to the light guide 131 through the rotary filter 410 is switched.

Figure 3:
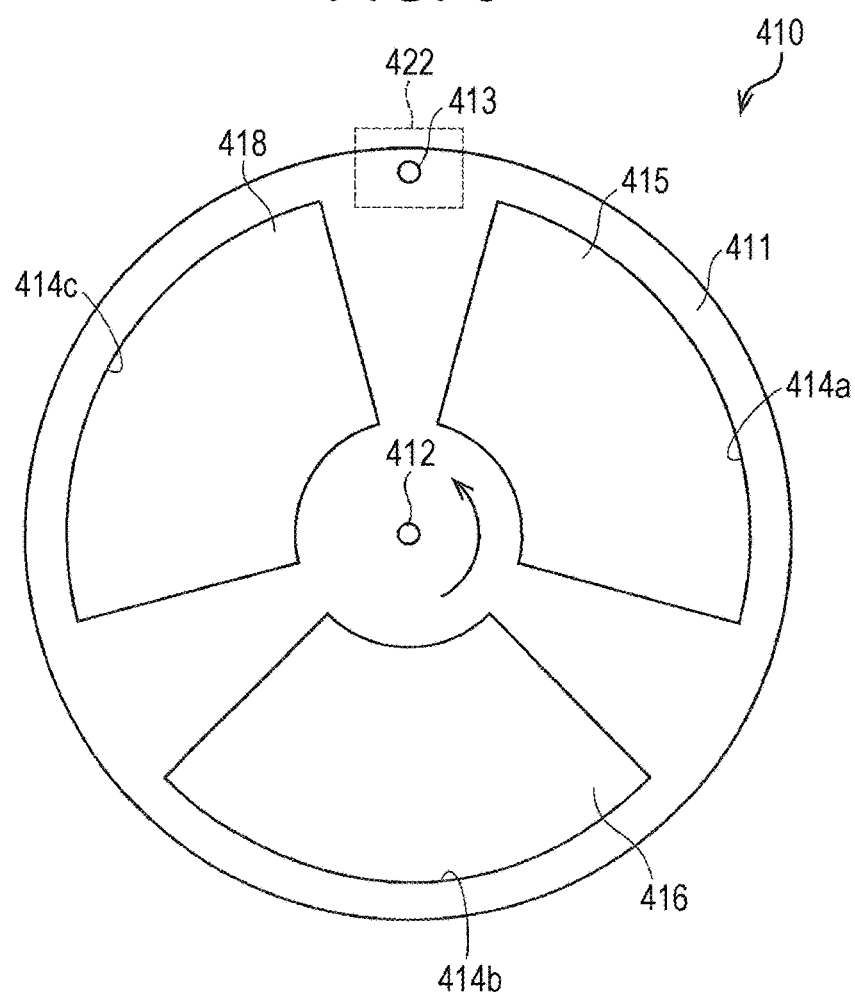
FIG. 3 is an external view (front view) of an example of a rotary filter used in a light source device of one embodiment.

FIG. 3 is an external view (front view) of the rotary filter 410. The rotary filter 410 includes a substantially disk-shaped frame 411 and three fan-shaped optical filters 415, 416, and 418. Three fan-shaped windows 414a, 414b, and 414c are formed at equal intervals around a central axis of the frame 411, and the optical filters 415, 416, and 418 are fitted in the windows 414a, 414b, and 414c, respectively. Note that, although the optical filters 415, 416, and 418 are dielectric multilayer film filters, in other embodiments, optical filters of other systems (for example, an absorption type optical filter, an etalon filter using a dielectric multilayer film as a reflecting film and the like) may also be used.

A boss hole 412 is formed on the central axis of the frame 411. An output shaft of a servomotor not illustrated of the filter control unit 420 is inserted in the boss hole 412 to be fixed, and the rotary filter 410 rotates together with the output shaft of the servo motor.

When the rotary filter 410 rotates in a direction indicated by an arrow in FIG. 3, the optical filter on which the light is incident is switched in the order of the optical filters 415, 416, and 418, so that the wavelength band of the illumination light IL passing through the rotary filter 410 is sequentially switched.

Figure 4:
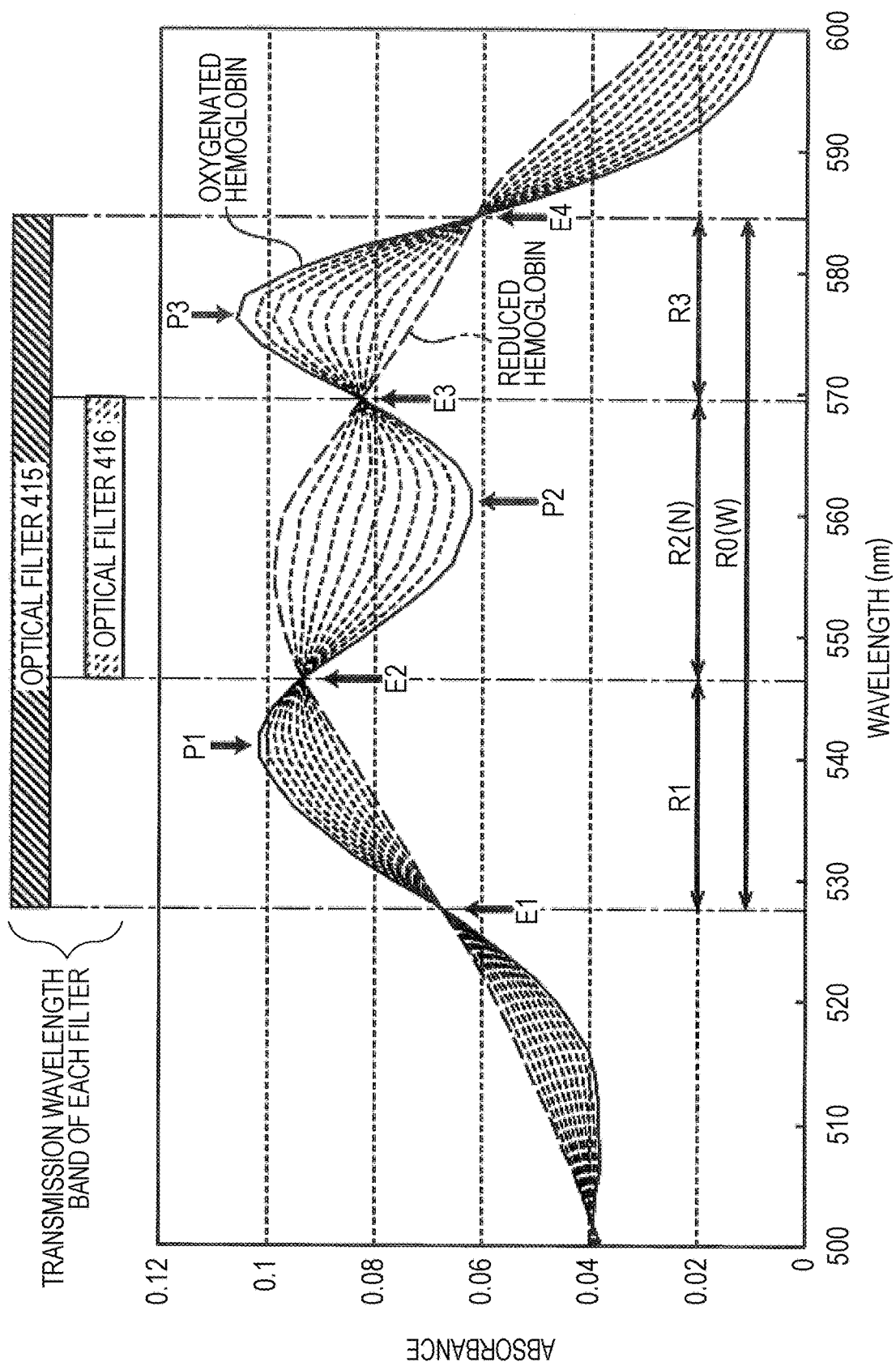
FIG. 4 is a view illustrating an example of an absorption spectrum of hemoglobin in the vicinity of 550 nm.

The optical filters 415 and 416 are optical band pass filters which selectively allow the light in the 550 nm band to pass. As illustrated in FIG. 4, the optical filter 415 is configured to allow light in a wavelength band R0 (W band) between isosbestic points E1 and E4 to pass with low loss and block light in other wavelength regions. In addition, the optical filter 416 is configured to allow light in a wavelength band R2 (N band) between isosbestic points E2 and E3 to pass with low loss and block light in other wavelength regions.

Also, the optical filter 418 is an ultraviolet cut filter, and in a visible light wavelength region, the light emitted from the light source lamp 430 passes through the optical filter 418. The light passing through the optical filter 418 is used as white light WL for imaging a normal observation image. Note that the window 414c of the frame 411 may be opened without using the optical filter 418.

Therefore, the light passing through the optical filter 415 out of the light emitted from the light source lamp 430 is hereinafter referred to as "Wide light", the light passing through the optical filter 416 out of the light emitted from the light source lamp 430 is hereinafter referred to as "Narrow light", and the light passing through the optical filter 418 out of the light emitted from the light source lamp 430 is hereinafter referred to as white light WL.

As illustrated in FIG. 4, a wavelength band R1 is a band including a peak wavelength of an absorption peak P1 derived from oxygenated hemoglobin, the wavelength band R2 is a band including a peak wavelength of an absorption peak P2 derived from reduced hemoglobin, and a wavelength band R3 is a band including a peak wavelength of an absorption peak P3 derived from oxygenated hemoglobin. Also, in the wavelength band R0, each peak wavelength of the three absorption peaks P1, P2, and P3 is included. Note that FIG. 4 is a view illustrating an example of an absorption spectrum of hemoglobin in the vicinity of 550 nm.

Also, the wavelength band R0 of the optical filter 415 and the wavelength band R2 of the optical filter 416 are included in a passing wavelength band (FIG. 2) of the G color filter of the color filter 141a. Therefore, the image of the living tissue T formed by the light passing through the optical filter 415 or 416 is obtained as an image of the G component of the color image data imaged by the imaging element 141.

A through hole 413 is formed on a peripheral edge of the frame 411. The through hole 413 is formed at the same position (phase) as a boundary between the window 414a and the window 414c in a rotation direction of the frame 411. A photo interrupter 422 for detecting the through hole 413 is arranged around the frame 411 so as to enclose a part of the peripheral edge of the frame 411. The photo interrupter 422 is connected to the filter control unit 420.

In this manner, the light source device 400 of this embodiment preferably includes a configuration of emitting the lights of different wavelength bands, that is, the Wide light, Narrow light, and white light WL as the illumination light IL by sequentially switching a plurality of optical filters 415, 416, and 418 in the optical path of the light emitted by the light source lamp 430.

(Calculation of Feature Amount of Living Tissue)

The feature amount of the living tissue T is calculated by the feature amount obtaining unit 510 of the image processing unit 500. A process of calculating the amount of hemoglobin and oxygen saturation Sat of hemoglobin of the living tissue T as the feature amounts from the image of the imaged living tissue T is described below.

As illustrated in FIG. 4, hemoglobin has a strong absorption band referred to as a Q band derived from porphyrin near 550 nm. The absorption spectrum of hemoglobin varies depending on the oxygen saturation Sat representing a proportion of oxygenated hemoglobin HbO in total hemoglobin. A solid line waveform in FIG. 4 indicates the absorption spectrum of oxygenated hemoglobin HbO with the oxygen saturation Sat of 100%, and a long broken line waveform indicates the absorption spectrum of reduced hemoglobin Hb with the oxygen saturation Sat of 0%. A short broken line is an absorption spectrum of hemoglobin at intermediate oxygen saturation Sat of 10, 20, 30, . . . 90%, that is, a mixture of oxygenated hemoglobin HbO and reduced hemoglobin Hb.

As illustrated in FIG. 4, oxygenated hemoglobin HbO and reduced hemoglobin Hb have different peak wavelengths in the Q band. Specifically, oxygenated hemoglobin HbO has the absorption peak P1 near a wavelength of 542 nm and the absorption peak P3 near a wavelength of 576 nm. On the other hand, reduced hemoglobin Hb has the absorption peak P2 near 556 nm. FIG. 4 illustrates the absorption spectrum when the sum of concentrations of oxygenated hemoglobin HbO and reduced hemoglobin Hb is constant, so that the isosbestic points E1, E2, E3, and E4 appear at which absorbance is constant regardless of a ratio of oxygenated hemoglobin HbO and reduced hemoglobin Hb, that is, the oxygen saturation. In the following description, the wavelength band between the isosbestic points E1 and E2 is the wavelength band R1 described above with the rotary filter 410, the wavelength region between the isosbestic points E2 and E3 is the wavelength band R2, the wavelength band between the isosbestic points E3 and E4 is the wavelength band R3, and the wavelength band between the isosbestic points E1 and E4, that is, the band obtained by combining the wavelength bands R1, R2, and R3 is the wavelength band R0. Therefore, the wavelength band of the Wide light which is the transmitted light transmitted through the optical filter 415 out of the light emitted from the light source lamp 430 is the wavelength band R0, and the wavelength band of the Narrow light which is the transmitted light transmitted through the optical filter 416 out of the light emitted from the light source lamp 430 is the wavelength band R2.

As illustrated in FIG. 4, absorption of hemoglobin increases or decreases linearly with respect to the oxygen saturation in the wavelength bands R1, R2, and R3. Specifically, absorption AR1 and AR3 of hemoglobin in the wavelength bands R1 and R3 increase linearly with respect to the concentration of oxygenated hemoglobin, that is, the oxygen saturation. In addition, absorption AR2 of hemoglobin in the wavelength band R2 linearly increases with respect to the concentration of reduced hemoglobin.

Herein, the oxygen saturation is defined by following expression (1).

Expression (1):

$$Sat = \frac{[HbO]}{[Hb] + [HbO]} \quad \text{[Expression 1]}$$

wherein
Sat: oxygen saturation
[Hb]: concentration of reduced hemoglobin
[HbO]: concentration of oxygenated hemoglobin, and
[Hb]+[HbO]: amount of hemoglobin (tHb).

Expressions (2) and (3) representing the concentrations of oxygenated hemoglobin HbO and reduced hemoglobin Hb are obtained from expression (1).

Expression (2):

$$[HbO] = Sat \cdot ([Hb] + [HbO]) \quad \text{[Expression 2]}$$

Expression (3):

$$[Hb] = (1 - Sat) \cdot ([Hb] + [HbO]) \quad \text{[Expression 3]}$$

Therefore, the absorption AR1, AR2, and AR3 of hemoglobin are feature amounts dependent on both the oxygen saturation and the amount of hemoglobin.

Herein, it is found that a total value of the absorbance in the wavelength band R0 does not depend on the oxygen saturation Sat but is a value determined by the amount of hemoglobin. Therefore, it is possible to quantify the amount of hemoglobin on the basis of the total value of the absorbance in the wavelength band R0. Also, the oxygen saturation Sat may be quantified on the basis of the total value of the absorbance in the wavelength band R1, the wavelength band R2, or the wavelength band R3, and the amount of hemoglobin quantified on the basis of the total value of the absorbance in the wavelength band R0.

The feature amount obtaining unit 510 of this embodiment includes a hemoglobin amount calculating unit 510a which calculates and obtains the amount of hemoglobin of the living tissue T on the basis of a first ratio to be described later which is sensitive to a change in the amount of hemoglobin of the living tissue T, and an oxygen saturation calculating unit 510b which calculates and obtains the oxygen saturation of hemoglobin of the living tissue T on the basis of a second ratio to be described later which is sensitive to a change in the oxygen saturation of hemoglobin.

Since a value of a luminance component of the color image data of the living tissue T illuminated with the Wide light (light of the wavelength band R0 passing through the optical filter 415) corresponds to the total value of the absorbance in the wavelength band R0 describe above, the hemoglobin amount calculating unit 510a of the feature amount obtaining unit 510 in this embodiment calculates the amount of hemoglobin on the basis of the luminance component of the color image data of the wavelength band R0. Herein, the luminance component may be calculated by multiplying the R component of the color image data by a predetermined coefficient, multiplying the G component of the color image data by a predetermined coefficient, multiplying the value of the B component of the color image data by a predetermined coefficient, and summing multiplied results.

Specifically, the hemoglobin amount calculating unit 510*a* of the feature amount obtaining unit 510 calculates the amount of hemoglobin on the basis of a ratio Wide(Yh)/WL(R) or Wide(Yh)/{WL(R)+WL(G)} (first ratio) obtained by dividing a luminance component Wide(Yh) of the color image data (second color image data) of the living tissue T using the Wide light (second light) as the illumination light IL by a R component WL(R) of the color image data (first color image data) of the living tissue T using the white light WL (first light) as the illumination light or a total component WL(R)+WL(G) of an R component WL(R) and a G component WL(G). When calculating the amount of hemoglobin, the ratio Wide(Yh)/WL(R) or Wide(Yh)/{WL(R)+WL(G)} obtained by dividing the luminance component Wide(Yh) by WL(R) or {WL(R)+WL(G)} is used for eliminating change in spectral characteristic of the living tissue T by a degree of scattering of the illumination light IL on the surface of the living tissue T. Especially, a reflection spectrum of the living tissue T such as the gastrointestinal tract inner wall is susceptible to an influence of the wavelength characteristic of scattering of the illumination light by the living tissue T in addition to the wavelength characteristic of absorption by the components forming the living tissue T (specifically, absorption spectrum characteristic of oxygenated hemoglobin and reduced hemoglobin). The R component WL(R) of the color image data (first color image data) of the living tissue T using the white light WL (first light) as the illumination light IL or the total component WL(R)+WL(G) of the R component and the G component is not affected by the amount of hemoglobin or the oxygen saturation Sat of hemoglobin, and represents the degree of scattering of the illumination light IL in the living tissue T. Therefore, in order to eliminate the influence of scattering in the living tissue T of the illumination light IL from the reflection spectrum of the living tissue T, the wavelength band of the white light WL (reference light) is preferably set to include the wavelength band in which one of the components of the first color image data is not sensitive to a change in the amount of hemoglobin of the living tissue T. In addition to this, the wavelength band of the white light WL (reference light) is preferably set such that one of the components of the first color image data includes a wavelength band not sensitive to the change in oxygen saturation. The wavelength band not sensitive to the change in the amount of hemoglobin of the living tissue T means that the value of the component of the wavelength band does not change even if the amount of hemoglobin changes.

According to one embodiment, a reference table representing a correspondence relationship between the information on the first ratio described above and the amount of hemoglobin in a living tissue having a known amount of hemoglobin is stored in advance in the memory 512, and the hemoglobin amount calculating unit 510*a* of the feature amount obtaining unit 510 calculates the amount of hemoglobin on the basis of the value of the first ratio in the imaged color image data of the living tissue T by using the reference table.

In the calculation of the amount of hemoglobin in one embodiment, as the first ratio, the ratio Wide(Yh)/WL(R) or Wide(Yh)/{WL(R)+WL(G)} between the luminance component Wide(Yh) of the color image data (second color image data) of the living tissue T using the Wide light (second light) as the illumination light IL and the R component WL(R) of the color image data (first color image data) of the living tissue T using the white light WL (first light) as the illumination light IL or the total component WL(R)+WL(G) of the R component and the G component is preferably used, but in another embodiment, the G component Wide(G) is also preferably used in place of the luminance component Wide(Yh) of the color image data (second color image data) of the living tissue T using the Wide light (second light) as the illumination light IL.

Furthermore, as described above, the total value of the absorbance in the wavelength band R2 decreases as the oxygen saturation Sat increases, and the total value of the absorbance in the wavelength band R0 varies according to the amount of hemoglobin but is constant irrespective of the change in the oxygen saturation Sat, so that the oxygen saturation calculating unit 510*b* of the feature amount obtaining unit 510 calculates the oxygen saturation on the basis of a second ratio defined below. That is, the oxygen saturation calculating unit 510*b* of the feature amount obtaining unit 510 calculates a ratio Narrow(Yh)/Wide(Yh) between a luminance component Narrow(Yh) of the color image data (third color image data) of the living tissue T illuminated with the Narrow light being the light of the wavelength band R2 passing through the optical filter 416 and the luminance component Wide(Yh) of the color image data (second color image data) of the living tissue T illuminated with the Wide light (light of the wavelength band R0 passing through the optical filter 416) as the second ratio. On the other hand, a correspondence relationship representing a relationship between the amount of hemoglobin and a lower limit value of the second ratio at the oxygen saturation Sat=0% and an upper limit value of the second ratio Narrow(Yh)/Wide(Yh) at the oxygen saturation Sat=100% is obtained from a known sample and stored in advance in the memory 512. The oxygen saturation calculating unit 510*b* of the feature amount obtaining unit 510 uses the calculation result of the amount of hemoglobin obtained from the color image data generated by the imaging of the living tissue T and the above-described correspondence relationship to obtain the lower limit value and the upper limit value of the second ratio. Furthermore, the oxygen saturation calculating unit 510*b* calculates a position of the oxygen saturation Sat where the second ratio Narrow(Yh)/Wide(Yh) of the imaged living tissue T is present by using the fact that the oxygen saturation Sat linearly changes according to the second ratio between the obtained lower limit value and upper limit value. In this manner, the oxygen saturation calculating unit 510*b* of the feature amount obtaining unit 510 calculates the oxygen saturation Sat.

Also, according to another embodiment, it is also possible that the reference table representing the correspondence relationship between the amount of hemoglobin and the amount of the second ratio and the oxygen saturation Sat of hemoglobin is obtained from the known sample and stored in advance in the memory 512, and the oxygen saturation Sat of hemoglobin is calculated from the calculated second ratio with reference to the reference table.

In the above-described embodiment, the second ratio is used as the ratio between the luminance component Narrow(Yh) of the color image data (third color image data) of the living tissue T illuminated with the Narrow light and the luminance component Wide(Yh) of the color image data (second color image data) of the living tissue T illuminated with the Wide light, but in another embodiment, it is also possible to use the ratio between the G component Narrow(G) of the color image data (third color image data) of the living tissue T illuminated with the Narrow light and the G component Wide(G) of the color image data (second color image data) of the living tissue T illuminated with the Wide light.

Also, in the above-described embodiment, the Narrow light of the wavelength band R2 is used for illuminating the living tissue T in order to calculate the second ratio, but this is not limited to the Narrow light. According to another embodiment, for example, it is also possible to use the light of which wavelength band is the wavelength band R1 or the wavelength band R2 with the intention to utilize the wavelength band R1 or the wavelength band R2 in which the total value of the absorbance varies with the change in the oxygen saturation Sat. In this case, the filter characteristic of the optical filter 416 may be set to the wavelength band R1 or the wavelength band R2.

In this manner, in the above-described embodiment, in order to correctly calculate the oxygen saturation Sat, it is preferable that the wavelength band of the Narrow light (third light) is included in the wavelength band of the Wide light (second light). Also, the wavelength band of the Wide light (second light) is preferably set to include the wavelength band R0 in which one of the components of the second color image data, for example, the luminance component and the G component is sensitive to the change in the amount of hemoglobin but is not sensitive to the change in the oxygen saturation from a viewpoint of calculating the oxygen saturation Sat correctly. The wavelength band not sensitive to the change in the oxygen saturation means that the value of the component of the wavelength band does not change even if the oxygen saturation changes. The wavelength band of the Narrow light (third light) is preferably set to include the wavelength band R2 in which one of the components of the third color image data, for example, the luminance component and the G component is not sensitive to the change in the amount of hemoglobin in the living tissue T but is sensitive to the change in the oxygen saturation of the living tissue T from a viewpoint of calculating the oxygen saturation Sat correctly.

Also, the wavelength band of the white light WL (first light) is preferably set to include the wavelength band in which one of the components of the first color image data is not sensitive to the change in the amount of hemoglobin of the living tissue T from a viewpoint of removing the influence of the spectrum characteristic of the scattered light in the living tissue T.

Also, it is preferable that the above-described Wide light (second light) is filtered light of the white light WL (first light) obtained by transmitting the first wavelength band in the range of 500 nm to 600 nm, for example, the wavelength band between the isosbestic points E1 and E4 out of the wavelength band of the white light WL (first light) by one of the optical filters and Narrow light (third light) is filtered light of the white light WL (first light) obtained by transmitting the second wavelength band narrower than the first wavelength band in the range of the first wavelength band, for example, the wavelength band between the isosbestic points E2 and E3 by one of the optical filters.

Figure 5:
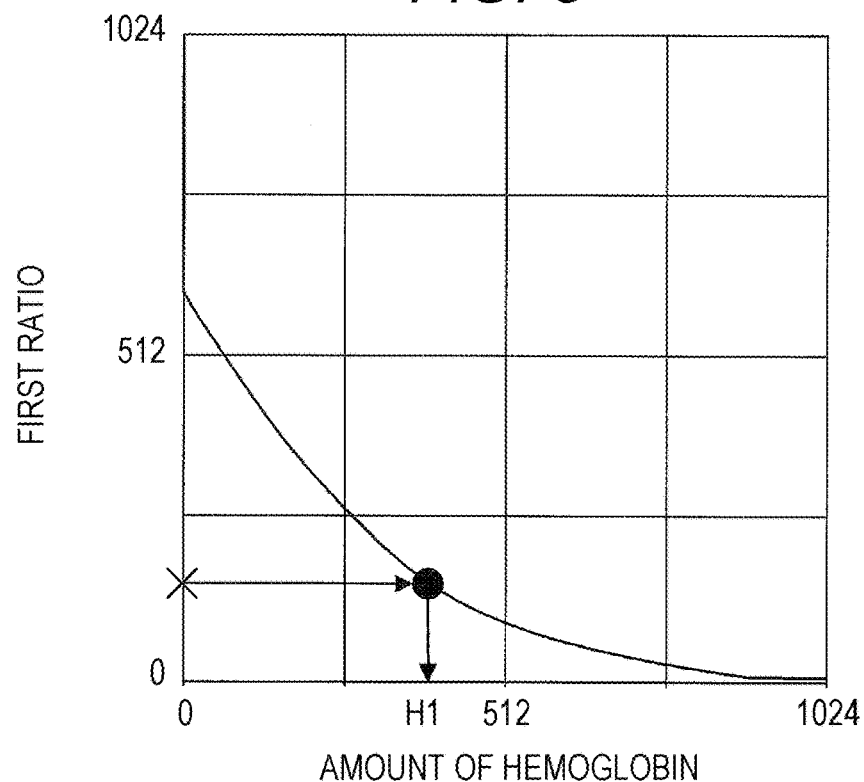
FIG. 5 is a view illustrating an example of a relationship between a first ratio and an amount of hemoglobin used in one embodiment.

FIG. 5 is a view illustrating an example of a relationship between the first ratio and the amount of hemoglobin. When obtaining the first ratio as described above, the hemoglobin amount calculating unit 510a of the feature amount obtaining unit 510 refers to the reference table representing the relationship as illustrated in FIG. 5 and obtains the amount of hemoglobin on the basis of the obtained first ratio. FIG. 5 illustrates that an amount of hemoglobin H1 is obtained on the basis of the value of the first ratio. Numerical values along the abscissa and ordinate in FIG. 5 are represented by values of 0 to 1024 for the sake of convenience.

Figure 6:
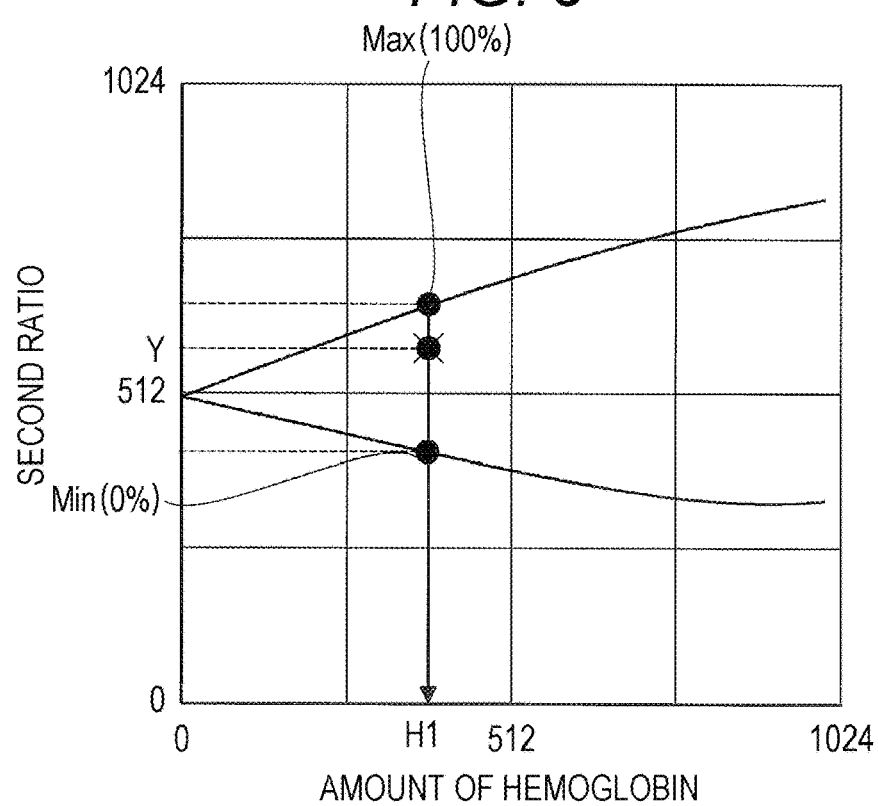
FIG. 6 is a view illustrating an example of a relationship between an upper limit value and a lower limit value of a second ratio and the amount of hemoglobin used in one embodiment.

FIG. 6 is a view illustrating an example of a relationship between the upper limit value and the lower limit value of the second ratio and the amount of hemoglobin. Numerical values along the abscissa and ordinate in FIG. 6 are represented by values of 0 to 1024 for the sake of convenience.

When obtaining the second ratio as described above, the oxygen saturation calculating unit 510b of the feature amount obtaining unit 510 obtains the upper limit value and the lower limit value of the second ratio in the obtained amount of hemoglobin by using the correspondence relationship illustrated in FIG. 6 on the basis of the amount of hemoglobin obtained by the hemoglobin amount calculating unit 510a and the second ratio. This upper limit value indicates the oxygen saturation Sat=100%, and the lower limit value indicates the oxygen saturation Sat=0%. By obtaining a position of the obtained second ratio between the upper limit value and the lower limit value, the oxygen saturation calculating unit 510b obtains the value of the oxygen saturation Sat. In FIG. 6, an upper limit value Max (100%) and a lower limit value Min (0%) when the amount of hemoglobin is H1 when the value of the second ratio is R2 are obtained. From a value Y of the second ratio between the upper limit value Max (100%) and the lower limit value Min (0%), the value of the oxygen saturation Sat is obtained.

Since the oxygen saturation Sat is obtained for each pixel of the image of the living tissue T, the distribution of the oxygen saturation Sat on the image of the living tissue T may be represented as the oxygen saturation distribution image. The oxygen saturation distribution image is represented by gradation display in which the color of the pixel is changed (for example, changed from red to blue) according to the value of the oxygen saturation Sat in each pixel. The oxygen saturation distribution image includes, for example, a distribution image of a part of the image of the living tissue T in which only the pixels within the oxygen saturation range determined in advance are displayed in a gradation manner.

Note that, in the above-described embodiment, as the Wide light and the Narrow light, the light of the wavelength band between the isosbestic points E1 and E4 within the range of the wavelength of 500 to 600 nm is used as illustrated in FIG. 4, but the wavelength band is not limited to this. Regarding the absorbance of hemoglobin, a large absorption peak exists in 420 to 450 nm in addition to the wavelength band near 500 to 600 nm, and the isosbestic point is also provided. Waveforms of the absorption spectrum of oxygenated hemoglobin and that of reduced hemoglobin are alternately switched around this isosbestic point. Therefore, in one embodiment, it is also preferable to calculate the amount of hemoglobin and the oxygen saturation using light of different wavelength or wavelength band within the wavelength band of 400 to 460 nm as the illumination light.

(Control of Display of Oxygen Saturation Distribution Image)

From the obtained oxygen saturation distribution image, the image display control unit 514 takes out the distribution (first distribution and second distribution) of the oxygen saturation within the oxygen saturation range determining the non-healthy site and within a plurality of types of oxygen saturation ranges and controls the display of the oxygen saturation distribution image so as to display each distribution so as to be superimposed on the image of the living tissue T. It is preferable that each of a plurality of types of oxygen saturation ranges corresponds to an oxygen saturation concentration range of each of a plurality of types of non-healthy sites, and further corresponds to the oxygen saturation concentration ranges of a plurality of types of lesions. That is, by utilizing the fact that the oxygen saturation range varies depending on the type of the non-healthy sites and further the lesions, the display 300 may identifiably display the image of distribution (first distribution and second distribution) of a plurality of types of non-healthy sites so as to be superimposed on the image of the living tissue T.

Hereinafter, it is described using two distributions which are the first distribution of the first non-healthy site which is the distribution of the oxygen saturation in the first oxygen saturation range and the second distribution of the second non-healthy site which is the distribution of the oxygen saturation in a second oxygen saturation range out of the distributions of the oxygen saturation within a plurality of types of oxygen saturation ranges.

Specifically, a portion in which the amount of hemoglobin in the position corresponding to each pixel in the oxygen saturation distribution image is equal to or larger than a predetermined amount and the oxygen saturation in the oxygen saturation distribution image is within the first oxygen saturation range is the first non-healthy site. A portion in which the amount of hemoglobin in the position corresponding to each pixel in the oxygen saturation distribution image is equal to or larger than a predetermined amount and the oxygen saturation in the oxygen saturation distribution image is within the second oxygen saturation range is the second non-healthy site. The portions may be distinguished from each other.

For example, when the first non-healthy site is the lesion of malignant tumor, the amount of hemoglobin in the first non-healthy site is equal to or larger than a predetermined amount and the oxygen saturation is several tens of % (for example, 20 to 30%), and when the second non-healthy site is a benign tumor site, the hemoglobin amount in this portion is equal to or larger than a predetermined amount and the oxygen saturation exceeds 30%, so that the distribution of the portion satisfying these conditions may be taken out separately as the first distribution and the second distribution. The image display control unit 514 sets in advance the oxygen saturation range of the non-healthy site likely to be malignant tumor such as cancer and the oxygen saturation range of the non-healthy site likely to be benign tumor. The image display control unit 514 determines whether the oxygen saturation range is satisfied and whether the amount of hemoglobin is equal to or larger than a predetermined amount, thereby determining whether there is the non-healthy site, and further a suspected site as the lesion for each pixel. In this case, according to one embodiment, the image display control unit 514 preferably takes out an area in which at least two or more pixels satisfying the oxygen saturation range are adjacent to each other. In the oxygen saturation distribution image, if only one pixel satisfying the oxygen saturation range is discontinuously present in isolation, this might be a noise component.

Display of the images of the first distribution and the second distribution so as to be identifiable on the display 300 may be any display as long as the images of the distributions may be identified, and a method of displaying is not especially limited. Since the oxygen saturation distribution image of the above-described embodiment is the image of gradation display in which hue changes in accordance with a level of the oxygen saturation, it is possible to identify only by the gradation display in which the hue changes by the value of the oxygen saturation when a plurality of types of oxygen saturation ranges (first oxygen saturation range and second oxygen saturation range) are not overlapped with each other. However, when the above-described oxygen saturation ranges (first oxygen saturation range and second oxygen saturation range) overlap with each other partially, it might be difficult to identify. In this case, according to one embodiment, in addition to the above-described gradation display to change the hue according to the level of the oxygen saturation, for example, it is also possible to display while changing identifiably the brightness, saturation, or transmissivity of the pixel for each distribution of the oxygen saturation range to be distinguished (first oxygen saturation range and second oxygen saturation range) and identifiably display the image of the distribution by edging an outline of the distribution with different colors.

As described above, the image display control unit 514 preferably takes out the image of the first distribution and the image of the second distribution so as to satisfy that the amount of hemoglobin in each pixel position of the image of the first distribution and the image of the second distribution is not smaller than the amount determined in advance. Since the blood is concentrated in the non-healthy site, especially in the lesion, it is preferable to exclude a part with a small amount of hemoglobin from a viewpoint of accurately extracting a suspected part as the non-healthy site and further as the lesion.

It is preferable that the image display control unit 514 takes out the image of the distribution (image of first distribution and image of second distribution) such that the amount of hemoglobin in a position corresponding to each pixel of the image of the first distribution and the image of the second distribution satisfies the range of the hemoglobin amount determined in advance (range of first hemoglobin amount and range of second hemoglobin amount) from a viewpoint of accurately taking out a suspected part of a plurality of types of non-healthy sites and further the lesions.

The image display control unit 514 preferably adjusts the transmissivity of the pixel displayed so as to be superimposed on the image of the living tissue T as for the pixel in which the value of the second ratio used for calculating the above-described oxygen saturation Sat is out of an allowable range (upper limit value and lower limit value) of the second ratio determined in accordance with the amount of hemoglobin. It is possible to prevent unnecessary information from being displayed as the image by adjusting the transmissivity of the pixel as for the pixel out of the allowable range.

Adjustment of the transmissivity of the pixel may be such that the transmissivity of the pixel located within the allowable range of the second ratio is set to 0% and the transmissivity of the pixel is gradually increased as a degree of deviation from the allowable range of the second ratio becomes larger in addition to the adjustment such that the transmissivity of the pixel located within the allowable range of the second ratio is set to 0% and the transmissivity of the pixel located in an area out of the allowable range of the second ratio is 100%.

Furthermore, even in a case where the second ratio is located within the allowable range of the second ratio determined according to the amount of hemoglobin, the transmissivity of the pixel is preferably adjusted as for the pixel out of a plurality of types of oxygen saturation ranges defining the non-healthy sites. As a result, it is possible to superimpose only the non-healthy site and further only the distribution of the portion suspected as the lesion on the image of the living tissue T to display. For example, it is preferable to make difference in transmissivity by making the transmissivity of the pixel of a portion out of the oxygen saturation range determined as the non-healthy site though the second ratio thereof is within the allowable range of the second ratio determined in accordance with the amount of hemoglobin lower than the transmissivity of the pixel the second ratio of which is out of the allowable range of the second ratio determined in accordance with the amount of hemoglobin.

Figure 7:
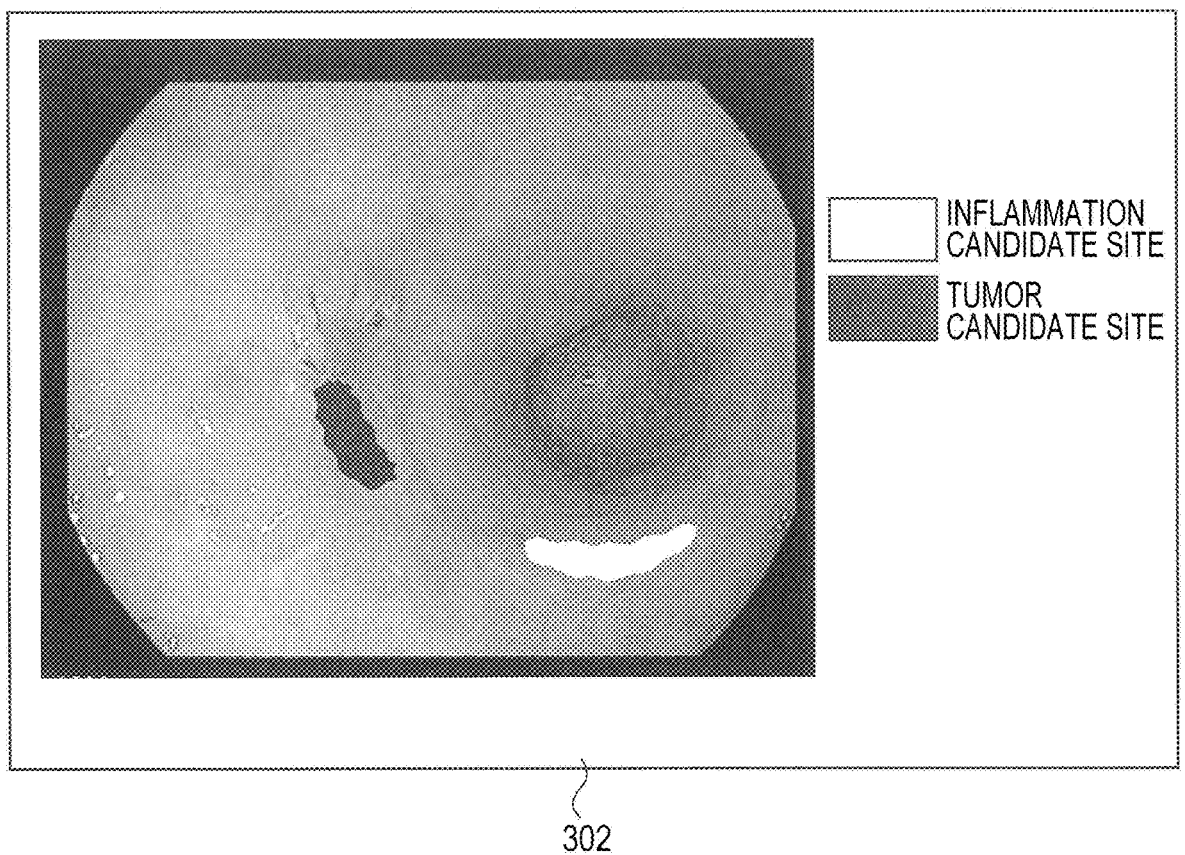
FIG. 7 is a view illustrating an example of display of an oxygen saturation distribution image according to one embodiment.

FIG. 7 is a view illustrating an example of display of the oxygen saturation distribution image displayed on a screen 302 of the display 300 according to this embodiment. As illustrated in FIG. 7, the image of the first distribution of the first non-healthy site ("inflammation candidate site") illustrating the distribution of the first oxygen saturation range and the image of the second distribution of the second non-healthy site ("tumor candidate site") illustrating the distribution of the second oxygen saturation range are displayed identifiably as the oxygen saturation distribution image. In the oxygen saturation distribution image, the pixels of images of the first distribution and the second distribution are non-transmission pixels with the transmissivity of 0% and the other pixels are transmission pixels with the transmissivity of 100% In the drawing, the image of the first distribution is illustrated as a single color white area, and the image of the second distribution is illustrated as a single color gray area. It goes without saying that it is also possible to color-code the images of the first distribution and the second distribution by gradation depending on the oxygen saturation. As described above, in the embodiment, each image of the distribution illustrating the distribution of a plurality of types of oxygen saturation ranges defining the non-healthy sites is displayed on the display 300 so as to be identifiable, so that it is possible to find a plurality of types of non-healthy sites by one observation and further it is possible to find a plurality of distributions of suspected sites as lesions by one observation.

Although the embodiment is described above, the present disclosure is not limited to the above-described configuration, and various modifications may be made within the scope of the technical idea of the present disclosure.

REFERENCE SIGNS LIST 1 endoscope system
100 electronic endoscope
110 insertion tube
111 insertion tube tip end
121 objective lens group
131 light guide
131a distal end
131b proximal end
132 lens
141 imaging element
141a color filter
142 cable
200 processor
300 display
400 light source unit
410 rotary filter
420 filter control unit
430 light source lamp
440 condenser lens
450 condenser lens
500 image processing unit
502 A/D converting circuit
504 pre-image processing unit
506 frame memory unit
508 post-image processing unit
510 feature amount obtaining unit
512 memory
514 image display control unit
516 controller

The invention claimed is:

1. An endoscope system comprising:
a light source device configured to emit at least two lights having different wavelength bands;
an endoscope including an imaging unit including an imaging element configured to generate color image data corresponding to each light by imaging a living tissue illuminated with the at least two lights;
a processor including a feature amount obtaining unit configured to calculate an amount of hemoglobin on a basis of a first ratio between components of the color image data, and further to calculate oxygen saturation of hemoglobin on a basis of a second ratio between the components of the color image data and the amount of hemoglobin to generate an oxygen saturation distribution image illustrating a distribution of the oxygen saturation of hemoglobin, and an image display control unit configured to control display of the oxygen saturation distribution image; and
an image display device configured to display the oxygen saturation distribution image so as to be superimposed on an image of the living tissue,
wherein the image display control unit is configured to take out an image of a first distribution of a first non-healthy site illustrating a distribution of first oxygen saturation ranges different from oxygen saturation of a healthy site and an image of a second distribution of a second non-healthy site illustrating a distribution of second oxygen saturation ranges different from the first oxygen saturation ranges and different from the oxygen saturation of the healthy site out of the generated oxygen saturation distribution image, and the image display control unit is further configured to adjust, to a first transmissivity, transmissivity of pixels each having a value of the second ratio out of an allowable range of the second ratio, the allowable range being determined according to the calculated amount of hemoglobin, and to adjust, to a second transmissivity lower than the first transmissivity, transmissivity of pixels each having a value of the second ratio within an allowable range of the second ratio and having the calculated oxygen saturation out of the first oxygen saturation ranges or the second oxygen saturation ranges, and
the image display device is configured to identifiably display the image of the first distribution and the image of the second distribution so as to be superimposed on the image of the living tissue as the oxygen saturation distribution image.

2. The endoscope system of claim 1,
wherein the at least two lights comprises at least three lights including first light, second light, and third light having different wavelength bands, and
the imaging unit is configured to generate first color image data corresponding to the first light, second color image data corresponding to the second light, and third color image data corresponding to the third light by imaging the living tissue illuminated with the first light, the second light, and the third light,
the feature amount obtaining unit includes a hemoglobin amount calculating unit configured to calculate the amount of hemoglobin on the basis of the first ratio between a component of the first color image data and a component of the second color image data and a oxygen saturation calculating unit configured to calculate the oxygen saturation of hemoglobin on a basis of the amount of hemoglobin and the second ratio between the component of the second color image data and a component of the third color image data.

3. An endoscope system comprising:
a light source device configured to emit at least two lights having different wavelength bands;
an endoscope including an imaging unit including an imaging element configured to generate color image data corresponding to each light by imaging a living tissue illuminated with the at least two lights;
a processor including a feature amount obtaining unit configured to calculate an amount of hemoglobin and oxygen saturation of hemoglobin in the living tissue by using a component of the color image data to generate an oxygen saturation distribution image illustrating a distribution of the oxygen saturation and an image display control unit configured to control display of the oxygen saturation distribution image; and
an image display device configured to display the oxygen saturation distribution image so as to be superimposed on the image of the living tissue,
wherein the image display control unit is configured to take out an image of a first distribution of a first non-healthy site illustrating a distribution of first oxygen saturation ranges different from oxygen saturation of a healthy site and an image of a second distribution of a second non-healthy site illustrating a distribution of second oxygen saturation ranges different from the first oxygen saturation ranges and different from the oxygen saturation of the healthy site from the distribution of the oxygen saturation as the oxygen saturation distribution image, the image of the first distribution and the image of the second distribution being taken out so as to satisfy a fact that the amount of hemoglobin in each pixel position of the image of the first distribution and the image of the second distribution is equal to or larger than an amount determined in advance, and
the image display device is configured to identifiably display the image of the first distribution and the image of the second distribution so as to be superimposed on the image of the living tissue as the oxygen saturation distribution image.

4. The endoscope system according to claim 3, wherein the feature amount obtaining unit includes a hemoglobin amount calculating unit which calculates the amount of hemoglobin on a basis of a first ratio between components of the color image data of the living tissue illuminated with different lights and an oxygen saturation calculating unit configured to calculate the oxygen saturation of hemoglobin on a basis of a second ratio between the components of the color image data and the amount of hemoglobin.

5. The endoscope system according to claim 3, wherein the light source device is configured to emit at least three lights including first light, second light, and third light having different wavelength bands,
the imaging unit is configured to generate first color image data corresponding to the first light, second color image data corresponding to the second light, and third color image data corresponding to the third light by imaging the living tissue illuminated with the first light, the second light, and the third light,
the feature amount obtaining unit includes:
a hemoglobin amount calculating unit configured to calculate the amount of hemoglobin on a basis of a first ratio between a component of the first color image data and a component of the second color image data; and
an oxygen saturation calculating unit configured to calculate the oxygen saturation of hemoglobin on a basis of the amount of hemoglobin and a second ratio between the component of the second color image data and a component of the third color image data.

6. The endoscope system according to claim 5, wherein the hemoglobin amount calculating unit is configured to calculate the amount of hemoglobin by using a ratio between a luminance component of the second color image data and an R component of the first color image data or a total component of the R component and a G component of the first color image data as the first ratio.

7. The endoscope system according to claim 5, wherein the oxygen saturation calculating unit is configured to calculate the oxygen saturation of hemoglobin on the basis of the second ratio and the amount of hemoglobin by using a ratio between a luminance component of the third color image data and the luminance component of the second color image data as the second ratio.

8. The endoscope system according to claim 5, wherein
a wavelength band of the first light is wider than a wavelength band of the second light and a wavelength band of the third light and the wavelength band of the second light is wider than the wavelength band of the third light, and
the wavelength band of the first light includes a wavelength band in which the component of the first color image data is not sensitive to a change in the amount of hemoglobin in the living tissue.

9. The endoscope system according to claim 5, wherein the wavelength band of the second light includes a wavelength band in which the component of the second color image data is sensitive to a change in the amount of hemoglobin of the living tissue but is not sensitive to a change in the oxygen saturation.

10. The endoscope system according to claim 5, wherein the wavelength band of the third light includes a wavelength band in which the component of the third color image data is not sensitive to a change in the amount of hemoglobin of the living tissue but is sensitive to a change in the oxygen saturation.

11. The endoscope system according to claim 5, wherein the second light is filtered light of the first light obtained by transmitting a first wavelength band within a range of 500 nm to 600 nm out of the wavelength band of the first light by an optical filter, and the third light is filtered light of the first light obtained by transmitting a second wavelength band narrower than the first wavelength band within a range of the first wavelength band by an optical filter.

12. A method of displaying an image, comprising:
emitting at least two lights having different wavelength bands;
generating color image data corresponding to each of the at least two lights by imaging a living tissue illuminated with the at least two lights;
using at least one component of the color image data to calculate a distribution of an oxygen saturation of hemoglobin in the living tissue;
generating an oxygen saturation distribution image from the distribution of the oxygen saturation of hemoglobin; and
identifiably displaying the oxygen saturation distribution image,
wherein the generating the oxygen saturation distribution image comprises obtaining, from the distribution of the oxygen saturation of hemoglobin, an image of a first distribution of a first non-healthy site and an image of a second distribution of a second non-healthy site, the image of the first distribution and the image of the second distribution being taken out so as to satisfy a fact that an amount of hemoglobin in each pixel position of the image of the first distribution and the image of the second distribution is equal to or larger than an amount determined in advance, and wherein the image of the first distribution of the first non-healthy site illustrates a distribution of the oxygen saturation of hemoglobin over a first range that is different from a range of the oxygen saturation of hemoglobin for a healthy site, and wherein the image of the second distribution of the second non-healthy site illustrates a distribution of the oxygen saturation of hemoglobin over a second range that is different from the first range and different from the range of the oxygen saturation of hemoglobin for the healthy site, and wherein the identifiably displaying the oxygen saturation distribution image includes superimposing, on an image of the living tissue, each of the image of the first distribution of the first non-healthy site and the image of the second distribution of the second non-healthy site.

13. The method of claim 12, wherein the using the at least one component of the color image data to calculate the distribution of the oxygen saturation of hemoglobin in the living tissue includes using at least one of the at least one component to calculate an amount of hemoglobin in the living tissue, wherein the calculated distribution of the oxygen saturation is based on the calculated amount of hemoglobin.

14. The method according to claim 13,
wherein the using the at least one component of the color image data to calculate the distribution of the oxygen saturation includes:
calculating the amount of hemoglobin on a basis of a first ratio between components of the color image data of the living tissue illuminated with different lights, and
calculating the oxygen saturation of hemoglobin on a basis of a second ratio between the components of the color image data and the amount of hemoglobin, and wherein the superimposing includes adjusting transmissivity of a pixel displayed so as to be superimposed on the image of the living tissue as for the pixel in which a value of the second ratio is deviated from an allowable range of the second ratio determined according to the amount of hemoglobin.

15. The method according to claim 13,
wherein the at least two lights comprises at least three lights including first light, second light, and third light having different wavelength bands, and
wherein the generating color image data comprises generating first color image data corresponding to the first light, second color image data corresponding to the second light, and third color image data corresponding to the third light by imaging the living tissue illuminated with the first light, the second light, and the third light, and
wherein the using the at least one component of the color image data to calculate the distribution includes:
calculating the amount of hemoglobin on a basis of a first ratio between components of the color image data of the living tissue illuminated with the first light and the second light, and
calculating the oxygen saturation of hemoglobin on a basis of the amount of hemoglobin and a second ratio between the components of the color image data of the living tissue illuminated with the second light and the third light, and
wherein the first ratio is the ratio between a component of the first color image data and a component of the second color image data, and
wherein the second ratio is the ratio between the component of the second color image data and a component of the third color image data.

* * * * *